US008460353B2

(12) United States Patent
Beran et al.

(10) Patent No.: US 8,460,353 B2
(45) Date of Patent: Jun. 11, 2013

(54) FLUID DISINFECTION UNIT FOR PATIENT TEMPERATURE CONTROL SYSTEM

(75) Inventors: Anthony V. Beran, Santa Ana, CA (US); Jerome B. Batta, Guilford, IN (US); Jacqueline C. Aronhalt, Loveland, OH (US)

(73) Assignee: Cincinnati Sub-Zero Products, Inc., Cincinnati, OH (US)

( * ) Notice: Subject to any disclaimer, the term of this patent is extended or adjusted under 35 U.S.C. 154(b) by 764 days.

(21) Appl. No.: 12/518,497

(22) PCT Filed: Dec. 13, 2007

(86) PCT No.: PCT/US2007/087412
§ 371 (c)(1),
(2), (4) Date: Nov. 12, 2009

(87) PCT Pub. No.: WO2008/076814
PCT Pub. Date: Jun. 26, 2008

(65) Prior Publication Data
US 2010/0076531 A1      Mar. 25, 2010

Related U.S. Application Data

(60) Provisional application No. 60/869,739, filed on Dec. 13, 2006.

(51) Int. Cl.
*A61F 7/00* (2006.01)
*C02F 1/32* (2006.01)
*A61L 2/00* (2006.01)

(52) U.S. Cl.
USPC ......... 607/104; 607/108; 210/748.11; 422/24

(58) Field of Classification Search
USPC .................. 607/104–112; 210/748.1, 748.11; 5/421–423; 422/22–24
See application file for complete search history.

(56) References Cited

U.S. PATENT DOCUMENTS

| 2,817,340 A | 12/1957 | Cuvier |
| 3,634,025 A | 1/1972 | Landry |

(Continued)

FOREIGN PATENT DOCUMENTS

| DE | 202004001194 | 4/2004 |
| GB | 763156 | 12/1956 |

(Continued)

OTHER PUBLICATIONS

Chinese Patent Office, Office Action, Jun. 23, 2010, English language translation (4 pgs.), Chinese language (4 pgs.).

(Continued)

*Primary Examiner* — Linda Dvorak
*Assistant Examiner* — Adam Avigan
(74) *Attorney, Agent, or Firm* — Wood, Herron & Evans, LLP

(57) ABSTRACT

A fluid disinfection unit [40] is incorporated into a patient warming/cooling system [10], to reduce the risk of bacteria buildup in the warming/cooling fluid, which is typically water. More particularly, a mobile housing [17] contains the operable components for circulating warming/cooling fluid to a patient [12], including a pump [23], a heating/cooling source [24], a reservoir [22], a controller [26] and a control panel [32] to assist a user in operating the components. The reservoir [22] has upper [22a] and lower [22b] sections, for replenishing water and circulating water, respectively. A UV source [40] is mounted so as to extend through both reservoir sections [22a, 22b], to simultaneously emit UV light into both sections during circulation of the warming/cooling fluid, thereby to disinfect the water contained therein. The UV source [40] includes a bulb [42] protected within a transparent cover [44] that is completely transparent, and has been treated so as to be shatterproof. A sensor [70] mounted to the housing [17] detects the UV emission level within the reservoir [22], and generates a signal to indicate the on/off status of the UV bulb [42], and/or the magnitude of the UV light within the reservoir [22].

12 Claims, 4 Drawing Sheets

U.S. PATENT DOCUMENTS

| | | | |
|---|---|---|---|
| 3,700,406 A | | 10/1972 | Landry |
| 3,837,800 A | | 9/1974 | Wood |
| 3,866,612 A | * | 2/1975 | Buker .................. 607/107 |
| 3,889,123 A | | 6/1975 | Bosshard |
| 3,894,236 A | | 7/1975 | Hazelrigg |
| 4,318,163 A | * | 3/1982 | Bryan .................. 362/359 |
| 4,336,223 A | * | 6/1982 | Hillman .................. 422/24 |
| 4,471,225 A | | 9/1984 | Hillman |
| 4,602,162 A | | 7/1986 | Sperry, III et al. |
| 4,694,179 A | | 9/1987 | Lew et al. |
| 4,769,131 A | | 9/1988 | Noll et al. |
| 4,968,437 A | | 11/1990 | Noll et al. |
| 4,971,687 A | | 11/1990 | Anderson |
| 5,074,322 A | | 12/1991 | Jaw |
| 5,304,213 A | | 4/1994 | Berke et al. |
| 5,626,768 A | | 5/1997 | Ressler et al. |
| 5,711,887 A | | 1/1998 | Gastman et al. |
| 5,742,063 A | | 4/1998 | Scroggins et al. |
| 6,083,387 A | | 7/2000 | LeBlanc et al. |
| 6,197,045 B1 | | 3/2001 | Carson |
| 6,299,761 B1 | | 10/2001 | Wang |
| 6,464,760 B1 | | 10/2002 | Sham et al. |
| 6,551,348 B1 | | 4/2003 | Blalock et al. |
| 6,602,409 B1 | | 8/2003 | Kuo |
| 6,623,706 B2 | | 9/2003 | Avnery |
| 6,656,424 B1 | | 12/2003 | Deal |
| 6,699,267 B2 | * | 3/2004 | Voorhees et al. ........... 607/104 |
| 6,773,608 B1 | | 8/2004 | Hallett et al. |
| 6,911,177 B2 | | 6/2005 | Deal |
| 6,966,937 B2 | | 11/2005 | Yachi et al. |
| 7,066,949 B2 | | 6/2006 | Gammons et al. |
| 7,377,935 B2 | * | 5/2008 | Schock et al. ........... 607/104 |
| 2003/0078638 A1 | | 4/2003 | Voorhees et al. |
| 2005/0258108 A1 | * | 11/2005 | Sanford .................. 210/748 |
| 2006/0163169 A1 | | 7/2006 | Eckhardt et al. |

FOREIGN PATENT DOCUMENTS

| | | |
|---|---|---|
| WO | 9626693 | 9/1996 |
| WO | 2004043313 | 5/2004 |
| WO | 2005110298 | 11/2005 |

OTHER PUBLICATIONS

International Search Report Forms: PCT/ISA/220, PCT/ISA/210, PCT/ISA/237, mailing date of Jun. 20, 2008.

European Patent Office, Office Communication, Supplementary European Search Report (7 pgs.), publication date Jun. 11, 2012.

* cited by examiner

FLUID DISINFECTION UNIT FOR PATIENT TEMPERATURE CONTROL SYSTEM

RELATED APPLICATION

This application claims priority to prior U.S. Provisional Patent Application No. 60/869,739, bearing the same title, which is expressly incorporated by reference herein, in its entirety.

This application claims the benefit of PCT Application No. PCT/US2007/087412, filed on Dec. 13, 2007, which claims the benefit of U.S. Provisional Patent Application No. 60/869,739, filed on Dec. 13, 2006.

FIELD OF THE INVENTION

This invention relates to patient temperature control, and more particularly, to a patient temperature control system and method that reduces susceptibility to contamination which can cause patient infection.

BACKGROUND OF THE INVENTION

It has long been suspected that infections acquired during a hospital stay are a major health care issue. Until recently hard data has not been available to demonstrate just how serious this problem has become. Pennsylvania was the first state to collect data tracking numbers and the results of hospital-acquired infections. The results are staggering.

For instance, applicants understand that this collected data shows that in 2004, at least 12,000 patients in Pennsylvania developed infections while in a hospital. Fifteen hundred, or about 12.5%, of those patients died. Two billion dollars in extra medical care was required to treat these patients. If these numbers are extrapolated to the rest of the U.S., nearly 100 patients are dying per day and an extra 50 billion dollars are being spent per year to fight hospital-acquired infections. The Center for Disease Control and Prevention estimates as many as two million infections are acquired in U.S. hospitals each year, resulting in approximately 90,000 deaths.

It is generally recognized that hypothermic patients are more susceptible to infection. Nonetheless, keeping the core body temperature properly regulated has grown to be the standard of care in almost every hospital and surgery center. An added benefit to keeping a patient properly regulated is the time required in Post Anesthesia Care Unit ("PACU") areas. When a patient moves from surgery through the PACU faster, more surgeries can be performed in the same amount of time. This makes each surgery more cost-effective.

One historical difficulty with medical patient temperature therapy is contamination. This issue exists for water systems as well as convective air systems, i.e. systems with closed loop fluid flow. For example, water based hypo-hyperthermia systems can be a perfect breeding ground for bacteria. Bacteria can also collect in convective warming devices. Almost all the air drawn into current version blowers gets filtered through HEPA level filtration. This is a great initial step for cleaning up the air that is provided to the patient. Nonetheless, poor maintenance practices can negate the overall effectiveness of these filters. Contaminates can enter the unit during maintenance or manufacturing, while the filter is removed. Contaminates can also enter the hose between uses. And once these contaminates have found their way into these types of devices, the warmed atmosphere may actually assist in their further growth. Applicant is aware of information that seems to indicate that a convective system may be to blame for elevated infection rates at a hospital in Denver.

Water based systems also have comparable challenges for staying safely clean. When a water based device is cleaned, it is not practical to expect that every part of the surface area that can harbor algae or bacteria will be properly exposed to disinfectants to sanitize the system. This is especially true when fundamental mistakes are made during the cleaning process. Often, the connecting water hoses are not cleaned. If a reusable water blanket is used, the internal surface of the blankets are often not cleaned sufficiently. So if these components are not clean to begin with, the circulating water will certainly not stay clean. Moreover, there are also known instances where the distilled water used in such devices arrived at the hospital in a contaminated condition. This contaminated water was then used in a clean device only to immediately inoculate the system with contaminates. In those situations, the components started out clean, but became contaminated by the water. So although patient temperature therapy is important for patient care, and also helps hospitals reduce overall surgery costs, there is an ongoing and important need to combat hospital infection. There is also an important need to come up with innovative ways to do that, because statistics show that existing procedures are not effective, for a variety of reasons.

Clearly, attempting to keep a warming system clean is a good practice. However, the only way to confidently supply germ-free and alga-free fluid to a patient receiving temperature therapy is to completely clean the fluid just before it comes in close proximity to the patient.

Unfortunately, due to personnel limitations and/or budget restrictions, it is all too common for the fluid circuit of a patient temperature control system to be cleaned either too infrequently or insufficiently. Even with proper cleaning protocols or manufacturer suggestions in place, the cleaning of the circulating fluid of a patient temperature control system will probably not be considered as important as it should be.

SUMMARY OF THE INVENTION

The present invention seeks to address these problems in a practical and straightforward manner. More particularly, the present invention incorporates a UV light source directly into upper and lower chambers of a reservoir that contains replenishing and circulating fluid that is circulating to a patient warming/cooling device, such as a blanket. By simultaneously directing UV light into both chambers of the reservoir, during operation, this system kills bacteria that can cause infection. This eliminates, or at least reduces, the time and labor associated with the need to disinfect the flow lines and the warming/cooling device (if reused), thereby reducing labor time and costs that would otherwise be needed to accomplish these often-neglected tasks. It also prevents, or reduces, the adverse effects caused in situations where distilled water arrives at the hospital in a contaminated state.

Preferably, the UV source includes a UV tube that is operatively connected to a control button at a control panel, for manual operation. The UV bulb may also be activated automatically upon the initiation of circulating fluid through the system. Preferably, the fluid is water, but it could be any other fluid with similar heat carrying capacity. The bulb resides with a tube shaped cover, which is preferably 100% transparent and shatterproof.

A sensor mounted in the reservoir senses the emitted UV light and is operatively connected to the control panel to indicate whether the UV light is activated. Depending on the circumstances, the sensor would provide a range of conditions, to show, for instance, lamp degradation, or the existence of blocking material or an obscuration in the line of sight from the sensor to the bulb (such as impurities attached to the lamp, or the sensor itself, or water impurities), or perhaps even the effects of water temperature.

Applicants' initial testing indicates that an "on" time of about 20 minutes is long enough to sufficiently kill bacteria in the water. Nonetheless, if desired, the UV source could be cycled on/off according to a different schedule or duration, or even controlled based on various inputs of the type described above.

The prior system was already configured to minimize the volume of water in the lower reservoir, compared to the upper reservoir, to optimize efficiency in warming or cooling the circulating water. This is achieved via a removable tray that divides the two reservoir chambers, but allows fluid communication therebetween. This existing structural layout was maintained for purposes of simplicity, but also used advantageously in positioning the UV source. More particularly, the cooling coil is already spaced away from the wall of the reservoir which has the inlet and outlets. By arranging the UV source adjacent to the outlet, in a direct line of sight, all fluid flowing outwardly from the lower reservoir flows through a relatively small volume portion of the lower reservoir which is close to and within the line of sight of the UV source. Thus, the structural orientation assures UV treatment of water flowing outwardly from the housing via the outlet.

The UV source mounts within a port formed in an upper cover which covers the top of the reservoir. A gasket plugs into the port, and is shaped to hold the tube-like cover. The UV bulb extends downwardly within the cover. Both the cover and the bulb extend down through a correspondingly sized opening formed in the tray, so that the UV light emitted from the bulb will traverse directly into the circulating water in both the upper and lower compartments.

The invention preferably uses water as the fluid for warming or cooling the patient. Nonetheless, it would be possible to use other liquids, or possibly even other non-liquid fluids, depending upon the particular situation.

These and other features will be more readily understood in view of the Figures and the following detailed description.

DETAILED DESCRIPTION OF A PREFERRED EMBODIMENT OF THE PRESENT INVENTION

Figure 1:
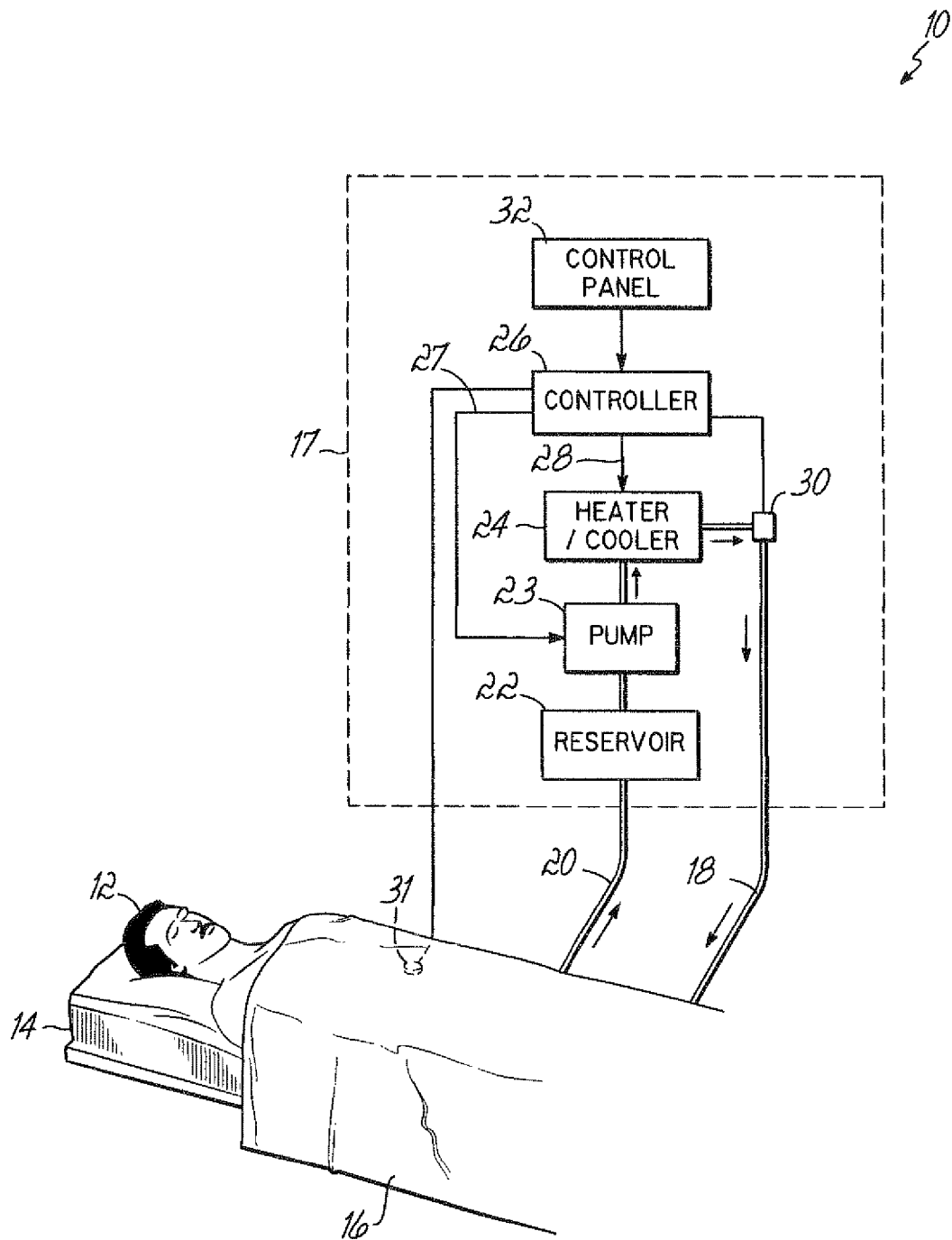
FIG. 1 is a schematic diagram which shows the general overall arrangement of the components used in the present invention.

FIG. 1 shows a schematic layout of a patient temperature control system 10 of the type applicable to this invention. This layout is meant to supply the proper background and context for explaining the details of the present invention. It is not meant to be limiting in scope. More particularly, FIG. 1 shows a patient 12 supported on a table 14, with a warming/cooling device, in this case a blanket 16, substantially covering the patient 12. Other types of devices could be used to transfer heating or cooling to the patient 12. Water flow lines interconnect the blanket 16 with a housing, shown by a dash line 17. More particularly, FIG. 1 shows an inflow conduit line 18 which routes circulating fluid, preferably water, to the blanket 16, and an outflow line 20 which routes the circulating water back to the housing 17.

Figure 3:
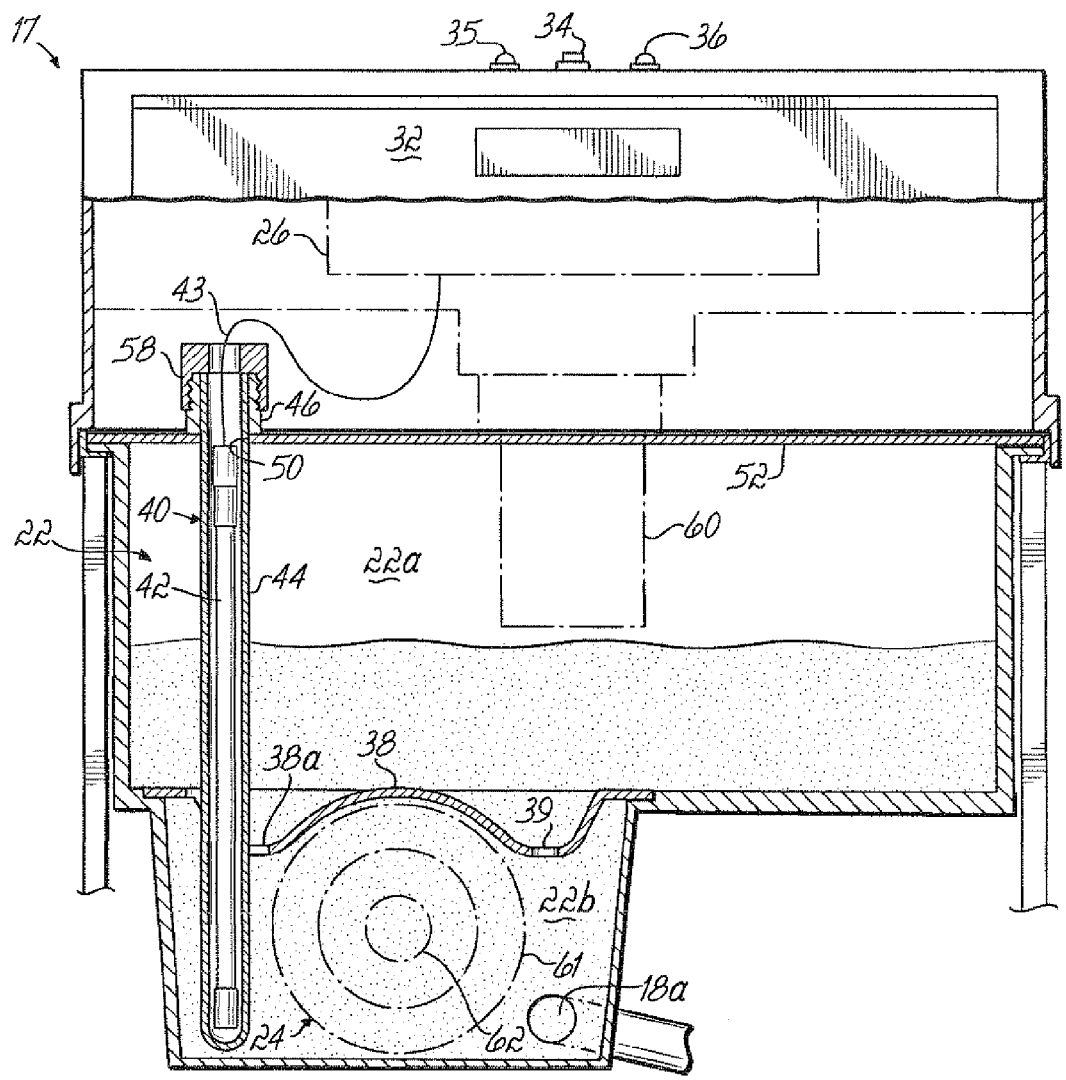
FIG. 3 is a cross sectional view taken along section lines 3-3 of FIG. 2.
Figure 4:
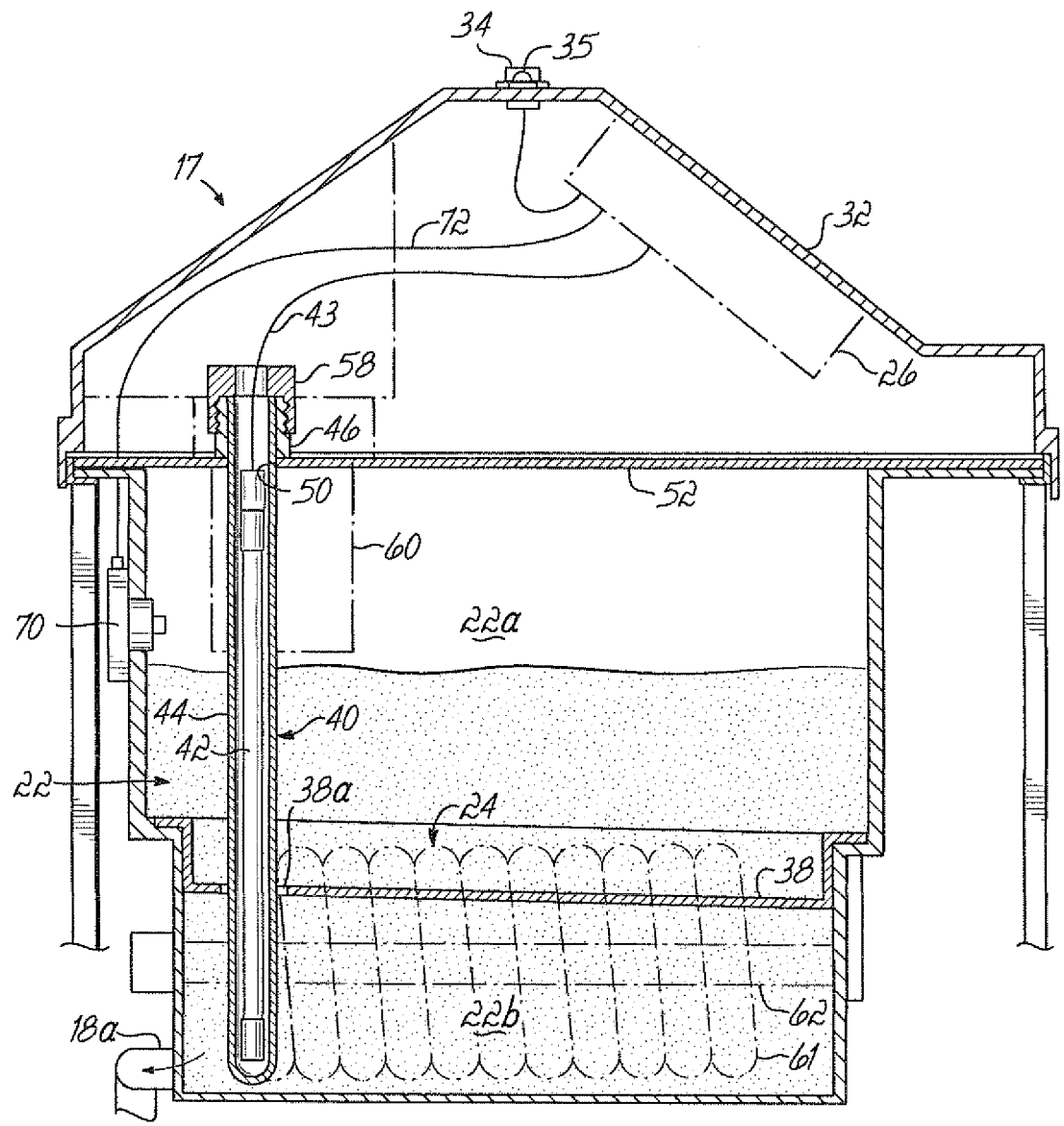
FIG. 4 is a cross sectional view taken along section lines 4-4 of FIG. 2.

Within housing 17, water from the outflow line 20 flows to a reservoir 22. From the tank, or reservoir 22, the circulating water flows to a pump 23, then through a heating/cooling device designated generally by reference numeral 24, and then outwardly again from the housing 17. The focus of the FIG. 1 is not on the particular details of the circulating water components residing within the housing 17, such as the reservoir 22, the pump 23, or the heating/cooling source 24. Rather, in FIG. 1 these components are shown generally in block form, for schematic purposes. FIG. 1 shows generally that these components are located with housing 17, not necessarily their structural relationship therein. FIGS. 3 and 4 better show the more specific structural relationships among these components.

FIG. 1 also shows a controller 26 residing within the housing 17. The controller 26 operatively connects to the heating/cooling source 24 via an electrical connector 27, and also to the pump 23 via an electrical connector 28. The controller 26 connects to a first temperature sensor 30 which senses the circulating water temperature as it exits the heating/cooling source 24, and also a second temperature sensor 31 which senses the body temperature of the patient 12. As with the circulating water components, the electrical connectors which connect to the components residing within housing 17 and with the temperature sensors 30 and 31 are merely shown in FIG. 1 in schematic form, to illustrate the general layout of the present invention. The controller 26 operatively connects to a control panel 32.

An operator selectively controls operation of the system 10 via pushbutton controls shown on the control panel 32. Stated another way, the controller 26 is microprocessor-based and configured to control warming and/or cooling in a manner which cooperates with the control panel 32 via the pushbuttons which are shown best in FIG. 2. The details of one manner of warming and/or cooling are described in more detail in assignee's published PCT Application Ser. No. PCT/US2006/041278, entitled "Patient Temperature System With Variable Gradient Warning/Cooling," which is expressly incorporated by reference herein, in its entirety. Also, this description relates to assignee's commercially available "Blanketrol III" ("B-III") system, which can treat up to three patients simultaneously.

Figure 2:
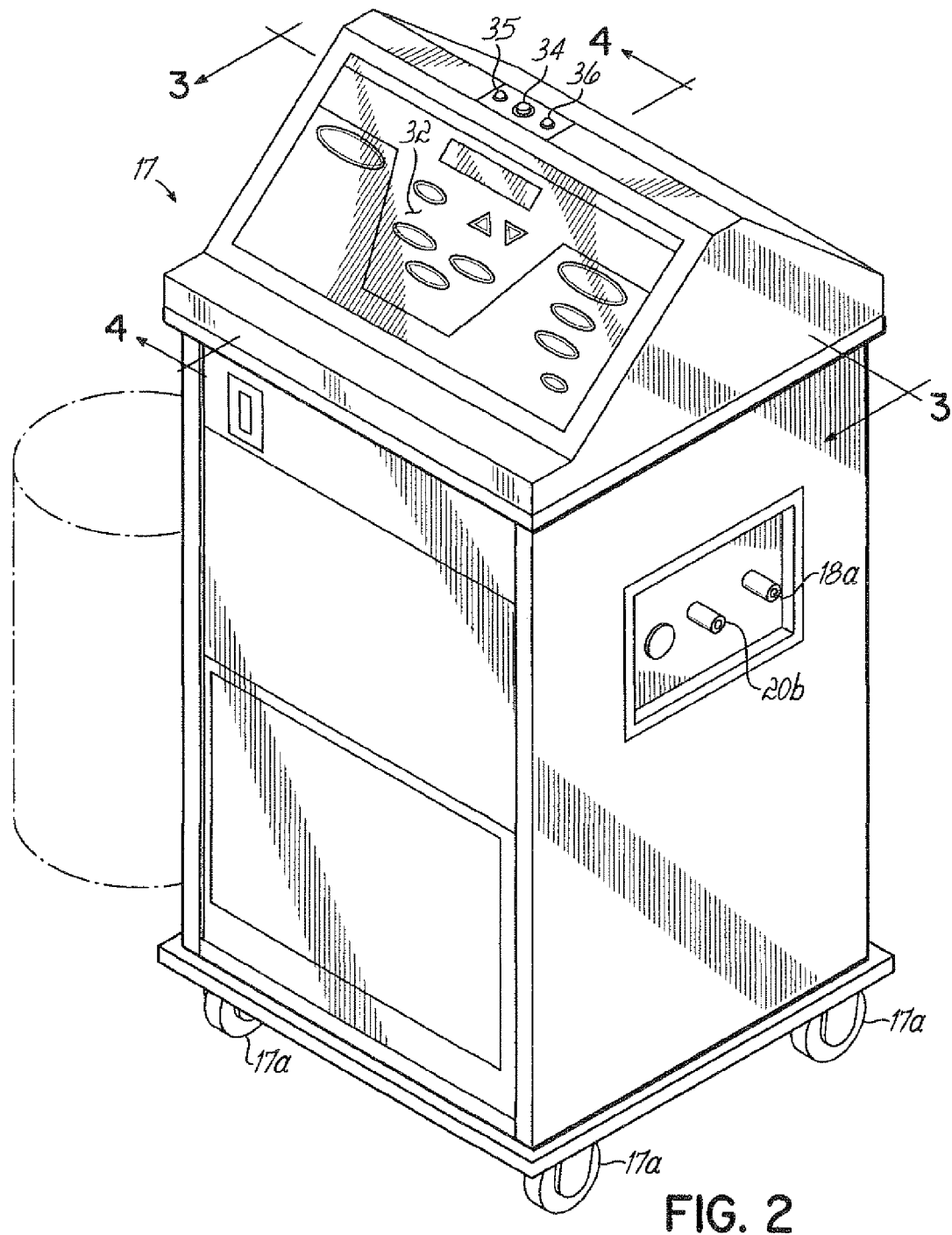
FIG. 2 is a perspective view of a wheel-supported housing which, according to a preferred embodiment of this invention, houses the disinfectant unit.

FIG. 2 shows housing 17 mounted on four wheels 17a, to facilitate mobility. FIG. 2 also shows an outlet 18a which is operatively connected to the inflow conduit line 18 ("inflow" relative to the device 16, namely, the blanket), and an inlet 20b which operatively connects to the outflow line 20. The control panel 32 at the top of housing 17 is angled for ease in viewing the controls and indicators mounted thereon.

At the top of control panel 32, FIG. 2 shows three additional controls related to the UV disinfectant unit of this invention. These controls are a pushbutton 34, to turn on the UV unit for a designated time period (not shown), an indicator light 35 to indicate if the UV unit is energized, i.e., on or off, and an indicator light 36 to identify if the UV bulb is emitting UV light, as described in more detail below. Other controls or indicators may be added, depending on the degree of control desired. However, there is also a certain degree of simplicity that is typically desired, to minimize the inconvenience to the operator.

More particularly, FIG. 3 shows reservoir, or tank, 22 in more detail, with an upper or replenishing reservoir 22a and a lower or circulating reservoir 22b. The upper and lower reservoirs 22a, 22b are defined by a removable tray 38. Tray 38 has at least one and preferably several holes 39 formed therein to allow for fluid communication, by gravity, between the upper 22a and lower 22b reservoirs.

FIG. 3 also Shows a UV source 40 mounted within reservoir 22. More particularly, UV source 40 includes a UV bulb 42 operatively connected to controller 26 via an electrical wire 43. Applicants have used a UV light bulb supplied by a company called Atlantic Ultra Violet, and particularly a 2.3 watt UV lamp referred to by Product No. 05-1119. But other wattages or bulbs could work, so long as sufficient dosage or magnitude of UV radiation is transmitted into the tank. There are also other considerations which weigh against overkill, or too much radiation. The goal is to effectively kill all bacteria in the water, and the dosage of UV light should be set accordingly. The bulb 42 resides within a longitudinal quartz tube, or cover, 44 for protection. The cover is preferably 100% transparent. Also, the tube 44 is preferably treated so as to be shatterproof, to enhance safety. Assignee has used Glass Surface Systems of Barberton, Ohio, to apply this shatterproof treatment, using this company's SUREGUARD® advanced coating technology. The coating that is applied to the cover is clear and cannot be seen unless the cover is cracked and then produces a spider-web-like appearance.

The cover 44 extends downwardly through upper reservoir 22a and into lower reservoir 22b, via a port 38a formed in the tray 38 to allow the tube cover 44 to extend downwardly therethrough. The top of the cover 44 resides within a gasket 46 that is aligned within and plugs into a port 50 formed in an upper sheet 52 which defines the top boundary of the reservoir 22. A hub 58 threadably connects to the gasket 46. Other mounting configurations would be equally suitable, so long as they provide: optimum line of sight emission of the UV light into both reservoir chambers 22a, 22b, optimum transparency of the cover 44, and enhanced safety to the operator, such as the shatterproof treatment. Preferably, the tube 44 and the UV lamp 42 have about the same length, to simultaneously operate effectively in both reservoirs 22a, 22b.

Phantom lines 60, 61, and 62 of FIG. 3 show a transverse cross sectional outline of some details of the structure which comprises the heating/cooling source 24, located downstream, of the fluid inlet 20a. Phantom lines 61 and 62 generally outline a cooling source, i.e., an encapsulated cooling coil. This is perhaps shown better if viewed in combination with FIG. 4, which also shows the relative sizes of lower reservoir 22b and upper reservoir 22a, i.e., lower reservoir 22b is smaller than that of upper reservoir 22a. This is due in part because the cooling element of heating/cooling source 24 forms the central part of lower reservoir 22b.

The tray 38 is arcuately shaped to accommodate these elements, and to minimize the volume below. As stated above, this optimizes cooling and heating efficiency. And again, this structure currently exists in assignee's commercially available B-III system. But this structure is also used to advantage with respect to this invention. More particularly, water generally flows from right to left, in FIG. 4 toward the outlet 18a. Notably, outlet 18a resides relatively close to the UV source 40, so that circulating water exiting the lower reservoir 22b necessarily flows past UV source 40 while en route to the outlet 18a. Also, the heating/cooling components 24 are spaced from the wall of the reservoir 22 in which the outlet 18a is formed. This structure helps assure that exiting fluid flows within a relatively small volume that is close to and within a line of sight of the UV bulb 42.

FIG. 4 also shows a sensor 70 mounted to a side wall of the reservoir 22, and directed at the UV source 40, along a line of sight path so as to detect the presence or absence of UV light within the reservoir 22. This sensor 70 operatively connects via electric line 72, to the controller, and also to indicator 36, to indicate whether the UV bulb 42 is emitting UV light. The indicator 36 will be unlit if the sensor emission is below a desired threshold, even though another indicating light, such as indicator 35, could be lit to indicate that power is being supplied to bulb 42. Moreover, as described above, the sensor 70 could be adapted to sense varying degrees of emission magnitude, or obscuration. Also, one or more additional sensors could be mounted in other locations, including below the normal liquid level, to gauge the distribution of emitted UV radiation, or one or both of the reservoirs chambers 22a, 22b. Also, the sensor 70 could be mounted so as to view through a "window" formed in a wall of the reservoir 22.

In operation, circulating fluid flows from the housing 17 to the blanket 16 that covers the patient 12, along line 18, and then back to the housing 17, and particularly to the reservoir 22. In the reservoir 22, depending on the number of devices 31 connected to the housing 17 (which could be up to three blankets) and due to pressure and volume fluctuations caused by, for instance, temporary flow line occlusions, the water level of the reservoir 22 may vary. Preferably, the water level extends into upper chamber 22a. The heated or cooled water flows, as needed, downwardly into the lower reservoir 22b and eventually to the outlet 18a, to again circulate to the patient 12. While the water resides within the reservoir 22, whether in the upper chamber 22a or the lower chamber 22b, the UV light emitted from UV source 40 kills water-bourne bacteria, thereby reducing the risk of infection to the patient and also to hospital personnel. This occurs for a predetermined time duration after start-up, for example 20 minutes. During this time, the indicator 35 shows that electrical power is being supplied to the bulb 42. Also, indicator 36 will be energized to indicate that sensor 70 is receiving or detecting UV light within the tank 22. Once the indicator 36 goes out, that indicates that the UV bulb 42 has burned out, or is emitting insufficient radiation to kill bacteria. In either case, the turning off of the indicator 36 indicates the need to replace the UV bulb 42.

Despite the statistics about infection described in the background, it has been only relatively recently that this risk of infection has been studied in depth and the results disseminated widely. For example, the invention is shown with respect to a patient warming/cooling system that is commonly used to induce hypothermia in a patient. There are other applicable uses for this invention. Nonetheless, when hypothermia is induced in a patient, the infection risk becomes higher, for several reasons. For instance, if by chance a nurse or a doctor, or perhaps a member of the patient's family, accidentally puts a hole in the water blanket while the blanket is being used to induce hypothermia in the patient, the results of cross contamination could be deadly for the patient. Therefore, for these types of systems it is even more important to control the infection that can be caused by fluid bourne bacteria. The germicidal cleaning provided by this invention essentially eliminates this risk.

Also, even though it has been known for some time, in other technologies, that UV light can be Used to disinfect fluids, including liquids, and other materials, applicants are not aware of any prior efforts to incorporate the benefits of this knowledge into a patient temperature control system, particularly of the type used to induce hypothermia in a patient. Prior to applicants' testing of this invention, applicants were not aware of any prior indications that germicidal treatment of circulating fluid, in this case the use of UV light to disinfect water, could be done in a safe, practical, and an effective manner within a hospital environment, for the treatment of multiple patients. Further complicating this situation is the fact that many plastics are not made to be used in the vicinity of ultraviolet light.

While this detailed description describes a preferred embodiment of the invention, those skilled in the art will understand that these specific details are not to be read into the claims. The invention contemplates, and those skilled in the art will understand, that the various components and parameters described above are subject to a reasonable degree of variation or modification, without departing from the spirit and scope of the invention.

We claim:

1. A patient temperature control system comprising:
 a fluid circuit for conveying cooling or warming fluid to a patient, to control the temperature of the patient;
 a cooling or warming device operatively connected to the fluid circuit and located adjacent the patient so as to provide a desired cooling or warming effect to the patient;
 a tank forming part of the fluid circuit, the tank serving as a source of supply fluid and holding extra fluid during an operational mode, the tank having a lower reservoir and an upper reservoir in fluid communication with the lower reservoir;
 a pump and a cooling or heating source forming part of the fluid circuit, the pump operable to cause the fluid to circulate in the fluid circuit to and from the cooling or warming device and the cooling or heating source operable to cool or heat the fluid as it circulates along the fluid circuit;
 a housing containing the tank, the pump, and the cooling or heating source;
 a UV source mounted to the tank and extending through the upper reservoir and into the lower reservoir; and
 a power source operatively connected to the UV source, the power source operable to activate the UV source to cause the UV source to direct UV radiation outwardly toward the fluid residing within the upper and lower reservoirs, thereby to disinfect the fluid contained therein.

2. The system of claim 1 wherein the fluid is water and the device is a blanket.

3. The system of claim 1 wherein the fluid circuit communicating with the lower reservoir is a closed loop.

4. The system of claim 1 and wherein the UV source further comprises:
 an elongated UV bulb; and
 an elongated tubular cover surrounding the UV bulb, the cover being transparent and shatterproof.

5. The system of claim 1 and further comprising:
 a sensor mounted on the housing in such manner as to have sensory access to the tank, thereby to sense the magnitude of UV radiation emitting from the UV source and to generate a corresponding signal.

6. The system of claim 1 and further comprising:
 a controller carried by the housing and operatively connected to the pump, the cooling or heating source, and to the UV source, and operable to control the operations thereof;
 a control panel operatively connected to the controller to facilitate a user's operation of the pump, the cooling or heating source, and the UV source;
 a sensor mounted on the housing in such manner as to have sensory access to the tank, thereby to sense the magnitude of UV radiation emitting from the UV source and to generate a corresponding signal; and
 an indicator operatively connected to the sensor and mounted at the control panel, the indicator operable to receive the corresponding signal and to indicate the magnitude of the sensed UV radiation.

7. The system of claim 1 wherein the tank includes an inlet for receiving fluid flowing from the device via the fluid circuit and an outlet for sending fluid to the device via the fluid circuit, the volume of the lower reservoir being relatively small compared to that of the upper reservoir, and the UV source being mounted proximate to and in a line-of-sight with the outlet, thereby to promote effective disinfecting of fluid that exits the lower reservoir via the outlet.

8. The system of claim 1 wherein at least a portion of the cooling or heating source is substantially surrounded by the lower reservoir.

9. The system of claim 1 wherein the UV source has a wattage sufficient to kill fluid-borne bacteria within a predetermined time window.

10. The system of claim 9 wherein the wattage of the UV source is in the range of about 2-3 watts and the predetermined time window is about 20 minutes.

11. A patient temperature control system comprising:
 a fluid circuit for conveying cooling or warming fluid to a patient, to control the temperature of the patient;
 a cooling or warming device operatively connected to the fluid circuit and located adjacent the patient so as to provide a desired cooling or warming effect to the patient;
 a tank forming part of the fluid circuit, the tank serving as a source of supply fluid and holding extra fluid during an operational mode, the tank having a lower reservoir and an upper reservoir in fluid communication with the lower reservoir;
 a pump and a cooling or heating source forming part of the fluid circuit, the pump operable to cause the fluid to circulate in the fluid circuit to and from the cooling or warming device and the cooling or heating source operable to cool or heat the fluid as it circulates along the fluid circuit;
 a housing containing the tank, the pump, and the cooling or heating source;
 a UV source mounted to the tank and extending through the upper reservoir and into the lower reservoir; and
 a power source operatively connected to the UV source, the power source operable to activate the UV source to cause the UV source to direct UV radiation outwardly toward the fluid residing within the upper and lower reservoirs, thereby to disinfect the fluid contained therein,
 wherein the tank further comprises: a removable tray defining a partition between the upper and lower reservoirs, the tray including at least one opening to permit fluid communication between the upper and lower reservoirs, the tray also including an opening through which the UV source extends.

12. A method of controlling a patient's temperature comprising:
 supplying warming or cooling fluid from a source to the patient via a device located adjacent to the patient and via a fluid circuit interconnecting the source and the device;
 disinfecting the warming or cooling fluid at the source, during the supplying step, thereby to also reduce the patient's susceptibility to contamination;
 disinfecting the warming or cooling fluid by emitting UV radiation through the warming or cooling fluid;
 sensing the emitted UV radiation and generating a signal in response thereto, for indicating the magnitude of the sensed UV radiation; and wherein the source comprises a tank having a lower reservoir, and an upper reservoir in fluid communication with the lower reservoir which replenishes the lower reservoir by gravity, and further comprising:
simultaneously emitting the UV radiation into the lower reservoir and the upper reservoir.

\* \* \* \* \*